(12) United States Patent
Moctezuma de la Barrera

(10) Patent No.: US 9,572,548 B2
(45) Date of Patent: *Feb. 21, 2017

(54) REGISTRATION OF ANATOMICAL DATA SETS

(71) Applicant: Stryker Leibinger GmbH & Co. KG, Freiburg (DE)

(72) Inventor: Jose Luis Moctezuma de la Barrera, Freiburg (DE)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 350 days.

This patent is subject to a terminal disclaimer.

(21) Appl. No.: 14/100,055

(22) Filed: Dec. 9, 2013

(65) Prior Publication Data

US 2014/0094694 A1 Apr. 3, 2014

Related U.S. Application Data

(63) Continuation of application No. 12/835,384, filed on Jul. 13, 2010, now Pat. No. 8,675,939.

(51) Int. Cl.
*G06K 9/00* (2006.01)
*A61B 5/05* (2006.01)
(Continued)

(52) U.S. Cl.
CPC ........... *A61B 8/5292* (2013.01); *A61B 5/1073* (2013.01); *A61B 5/1128* (2013.01); *A61B 6/032* (2013.01);
(Continued)

(58) Field of Classification Search
CPC ... A61B 8/5292; A61B 8/5223; A61B 8/0875; A61B 19/5244; A61B 8/12; A61B 5/1073
See application file for complete search history.

(56) References Cited

U.S. PATENT DOCUMENTS 5,572,999 A 11/1996 Funda et al.
5,690,106 A 11/1997 Bani-Hashemi et al.
(Continued)

FOREIGN PATENT DOCUMENTS

EP 1467317 10/2004
EP 01161194 4/2006
(Continued)

OTHER PUBLICATIONS

K. Tyryshkin, SPIE Medical Imaging, vol. 6141, pp. 61412L-1-61412L-8, San Diego, Feb 2006—A Novel Ultasound-guided shoulder arthroscopic surgery.
(Continued)

*Primary Examiner* — Sean Dougherty
(74) *Attorney, Agent, or Firm* — Howard & Howard Attorneys PLLC

(57) ABSTRACT

Methods and systems are disclosed for relating additional spatial information associated with one volume data set of an anatomical structure with another volume data set of the anatomical structure where the spatial information is not available. A unique spatial characteristic of the volume data set is identified, such as an image moment of inertia, and an arbitrary reference frame is assigned to the volume data set and correlated with the unique spatial characteristic. The additional spatial information is also correlated with the arbitrary reference frame. The additional spatial information is then correlated to a second volume data set of the anatomical structure by registering the first and second volume data sets based on the unique spatial characteristic. The methods and systems allow registration of different volume data sets of the same anatomical structure and transfer of the additional spatial information without establishing a local reference frame based on predefined landmarks.

27 Claims, 8 Drawing Sheets

(51) Int. Cl.

| | | |
|---|---|---|
| A61B 5/103 | (2006.01) | |
| A61B 5/117 | (2016.01) | |
| A61B 8/08 | (2006.01) | |
| G06F 19/00 | (2011.01) | |
| G06Q 50/22 | (2012.01) | |
| G06T 7/00 | (2006.01) | |
| A61B 5/107 | (2006.01) | |
| A61B 5/11 | (2006.01) | |
| A61B 6/03 | (2006.01) | |
| A61B 8/12 | (2006.01) | |
| A61B 8/00 | (2006.01) | |

(52) U.S. Cl.
CPC ............ *A61B 6/037* (2013.01); *A61B 8/0875* (2013.01); *A61B 8/12* (2013.01); *A61B 8/4254* (2013.01); *A61B 8/5223* (2013.01); *A61B 34/20* (2016.02); *A61B 90/30* (2016.02); *A61B 90/361* (2016.02); *G06F 19/321* (2013.01); *G06F 19/322* (2013.01); *G06Q 50/22* (2013.01); *G06T 7/0024* (2013.01); *A61B 2090/363* (2016.02); *A61B 2090/364* (2016.02); *A61B 2090/378* (2016.02); *G06T 2207/10072* (2013.01); *G06T 2207/30008* (2013.01)

(56) References Cited

U.S. PATENT DOCUMENTS

| | | | |
|---|---|---|---|
| 5,937,083 A | 8/1999 | Ostuni | |
| 6,201,984 B1 | 3/2001 | Funda et al. | |
| 6,205,411 B1 | 3/2001 | DiGioia, III et al. | |
| 6,625,607 B1* | 9/2003 | Gear | G06F 17/50 |
| 7,117,027 B2 | 10/2006 | Zheng et al. | |
| 7,570,791 B2 | 8/2009 | Frank et al. | |
| 7,929,745 B2 | 4/2011 | Walker et al. | |
| 7,949,179 B2 | 5/2011 | Ikeuchi et al. | |
| 7,968,851 B2 | 6/2011 | Rousso et al. | |
| 8,014,625 B2 | 9/2011 | Dewaele | |
| 8,036,441 B2 | 10/2011 | Frank et al. | |
| 8,121,362 B2 | 2/2012 | Zhan et al. | |
| 8,280,482 B2 | 10/2012 | Rusinek et al. | |
| 2004/0111024 A1 | 6/2004 | Zheng et al. | |
| 2005/0025354 A1* | 2/2005 | Macy | G06T 7/0004 382/154 |
| 2005/0027187 A1 | 2/2005 | Barth et al. | |
| 2005/0249398 A1 | 11/2005 | Khamene et al. | |
| 2005/0256398 A1 | 11/2005 | Hastings et al. | |
| 2006/0004275 A1 | 1/2006 | Vija et al. | |
| 2006/0074292 A1 | 4/2006 | Thomson et al. | |
| 2006/0120583 A1 | 6/2006 | Dewaele | |
| 2006/0133694 A1 | 6/2006 | Dewaele | |
| 2006/0262970 A1 | 11/2006 | Boese et al. | |
| 2007/0238952 A1 | 10/2007 | Boese et al. | |
| 2008/0033240 A1 | 2/2008 | Hoffman et al. | |
| 2008/0039713 A1 | 2/2008 | Thomson et al. | |
| 2008/0267483 A1 | 10/2008 | Zhan et al. | |
| 2008/0287781 A1 | 11/2008 | Revie et al. | |
| 2009/0076371 A1 | 3/2009 | Lang et al. | |
| 2009/0124890 A1 | 5/2009 | Derycke | |
| 2009/0232369 A1 | 9/2009 | Senegas et al. | |
| 2009/0290771 A1 | 11/2009 | Frank et al. | |
| 2009/0324093 A1* | 12/2009 | Miarecki | G06K 9/6206 382/203 |
| 2010/0080415 A1 | 4/2010 | Qureshi et al. | |
| 2011/0249882 A1 | 10/2011 | Bornfleth | |
| 2011/0305405 A1 | 12/2011 | Kawamura | |

FOREIGN PATENT DOCUMENTS

| | | |
|---|---|---|
| WO | 0054687 | 9/2000 |
| WO | 03086190 | 10/2003 |
| WO | 2006039009 | 4/2006 |
| WO | 2007047782 | 4/2007 |

OTHER PUBLICATIONS

Rasmussen et al., Acta Neurochir (2007) vol. 149, pp. 365-378, "Functional neuronavigation combined with intra-operative 3D ultrasound: intial experiences during surgical resections close to eloquent brain areas and future directions in automatic brain shift compensation of preoperative data".

Shao et al., Proc. SPIE (2005), vol. 5747, pp. 1263-1273—"Deformable Registration for Integration of MRI/MRSI Information in TRUS-guided Prostate Biopsy".

FA. Jolesz, Neurosurg Clin N. Am., (2005)—vol. 16(1) pp. 201-213—"Future Perspective for Intraoperative MRI".

Arbel et al., Comput Aided Surg. (2004)—vol. 9(4) pp. 123-136—"Automatic non-linear MRI-ultrasound Registration for the Correction of Intra-Operative Brain Deformations".

Firle et al., In Proceedings of SPIE (2004)—vol. 5370, pp. 1130-1138—"Mutual Information Based Registration for Ultrasound and CT Datasets".

Shao et al., ACTA Press, http://www.actapress.com/Abstract.aspx?paperId=18117, "Multimodal Image Registration of the Prostate Gland Using Surface-to-Volume Fitting".

Xie et al., Proc. Intern. Conf. Image Processing (ICIP), (2004)—vol. 4, pp. 2575-2578*"Shape Prior Based Segmentation for organ Deformation Correction".

Pujol et al., Proceedings of the 6th International Conference on Medical Image Computing and Computer Assistant Interventionl, (2003)—vol. 2879, pp. 231-238—"Minimally Invasive navigation for the Endovascular Treatment of Abdominal Aortic Aneurysm: Preclinical Validation of the Endovax System".

Gobbi et al., Proceedings of the 5th International Conference on Medical Image Computing and Computer-Assisted Intervention—Part II, (2002)—vol. 2489, pp. 156-163—"Interactive Intra-operative 3D Ultrasound Reconstruction and Visualization".

Gobbi et al., Proceedings of SPIE., (2001)—vol. 4319, pp. 264-271—"Correction of Pre-Operative MRI and Intra-Operative 3D Ultrasound to Measure Brain Tissue Shift".

Gobbi et al., Engineering in Medicine and Biology Society, (2000)—vol. 3, pp. 1738-1740—"Integration of Intra-Operative 3D Ultrasound with Pre-Operative MRI for Neurosurgical Guidance".

Gobbi et al., MICCAI, (2000), vol. 1935 pp. 106-114—"Ultrasound/MRI Overlay With Image Warping for Neurosurgery".

Gobbi et al., Medical Image Computing and Computer-Assisted Intervention. MICCAI 2nd International Conference Proceedings. (1999)—pp. 920-927—"Ultrasound Probe Tracking for Real-Time Ultrasound/MRI Overlay and Visualization of Brain Shift".

Muratore et al., Proc. SPIE, (1999)—vol. 3661, pp. 1499—1510—"Vertebral Surface Extraction from Ultrasound Image for Technology-guided Therapy".

Peters et al., SPIE, (1998)—vol. 3262, p. 244-252 Comprehensive Approach to Image-guided Surgery.

Leonard, J., IEEEXplore—(1998)—pp. 37-44—"Sensor Fusion for Surgical Application".

Maier et al., Proc. SPIE—(1997)—vol. 2976., p. 156-169—"Use of 3D Ultrasound and Image Matching in Computer-assisted Neuronavigation".

Reinertsen et al., Medical Image Analysis, (2007)—vol. 11.pp. 374-388—"Validation of Vessel-based Registration for Correction of Brain Shift".

Jain et al., Proc of SPIE. (2004)—vol. 5373, pp. 131-142—"Understanding Bone Responses in B-Mode Ultrasound Images and Automatic Bone Surface Extraction Using a Bayesian Probabilistic Framework".

Beek et al.,—Med Image Comput. Comput Assist Interv. —vol. 9(Pt2), pp. 536-543—"Ultrasound-guided percutaneous scaphoid pinning: operator variability and comparison with traditional fluoroscopic procedure".

F. Langlotz, (2002)—J. Vis. Comput. Animat.—vol. 13, pp. 77-78—"State-of-the-art in Orthopaedic Surgical Navigation with a Focus on Medical Image Modalities".

Woydt et al., (2001)—Neurol Res.—vol. 23(7), pp. 697-705—New Ultrasound Techniques and Their Application in Neurosurgical Intra-Operative Sonography.

(56) References Cited

OTHER PUBLICATIONS

Fichtinger et al., (2001)—Proceedings 30th Applied Imagery Pattern Recognition Workship (AIPR)—pp. 3-8—"The Surgical CAD/CAM Paradigm and an Implementation for Robotically-Assisted Percutaneous Local Therapy."

Shao et al., Multimodal Image Registration of the Prostate Gland Using Surface-To-Volume Fitting, Proceedings of the 6th IASTED International Conference, Aug. 23-25, 2004, pp. 395-400, Honolulu Hawaii, USA.

* cited by examiner

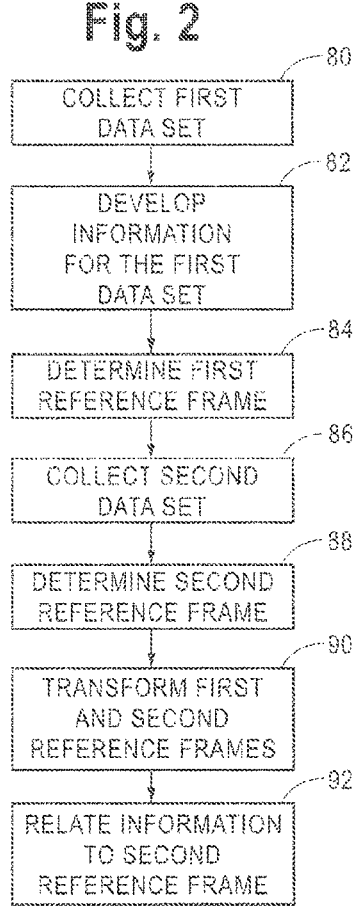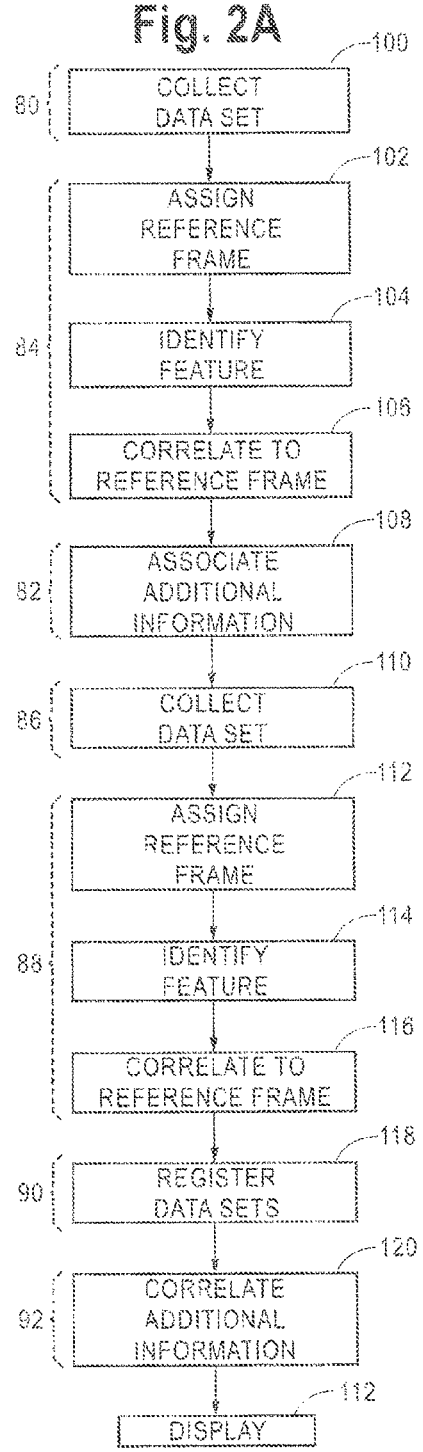

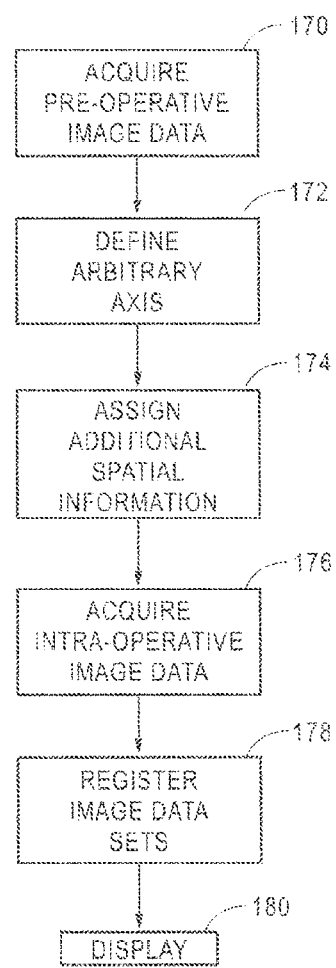

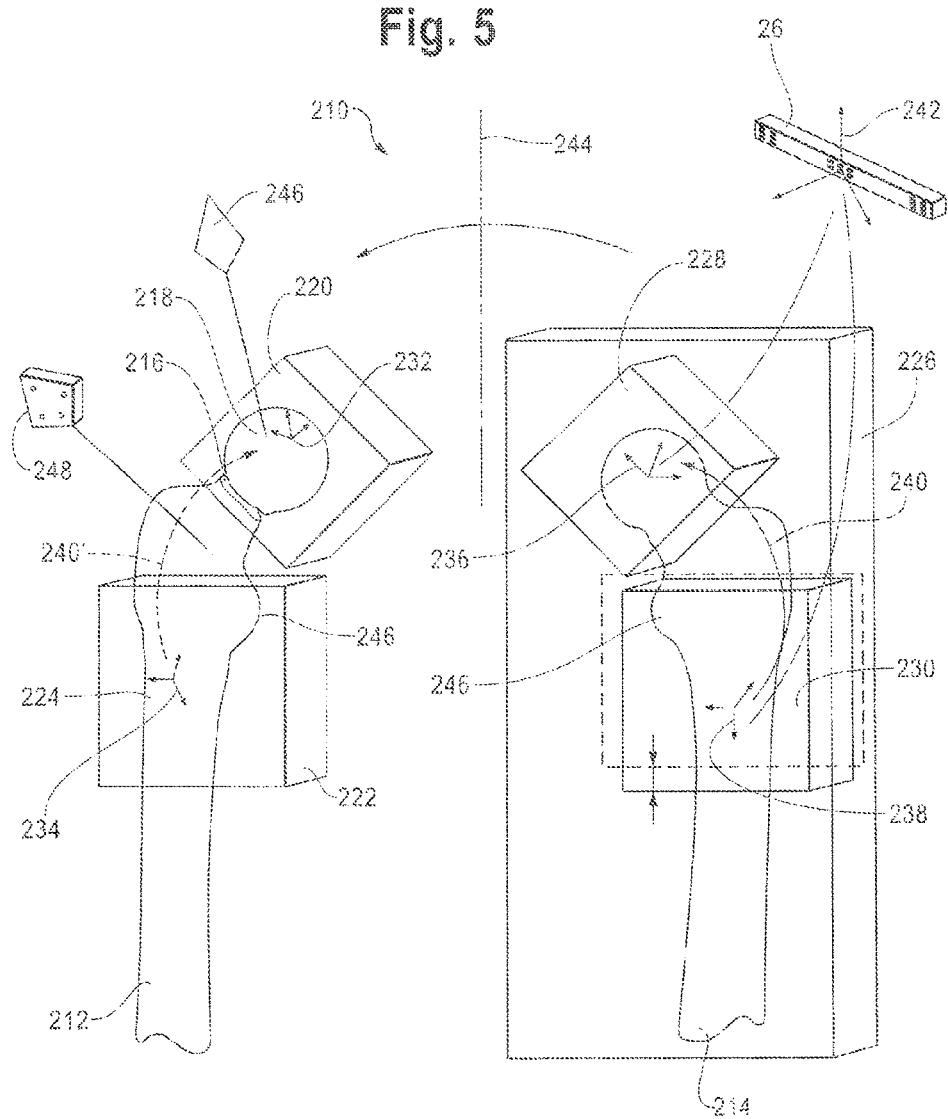

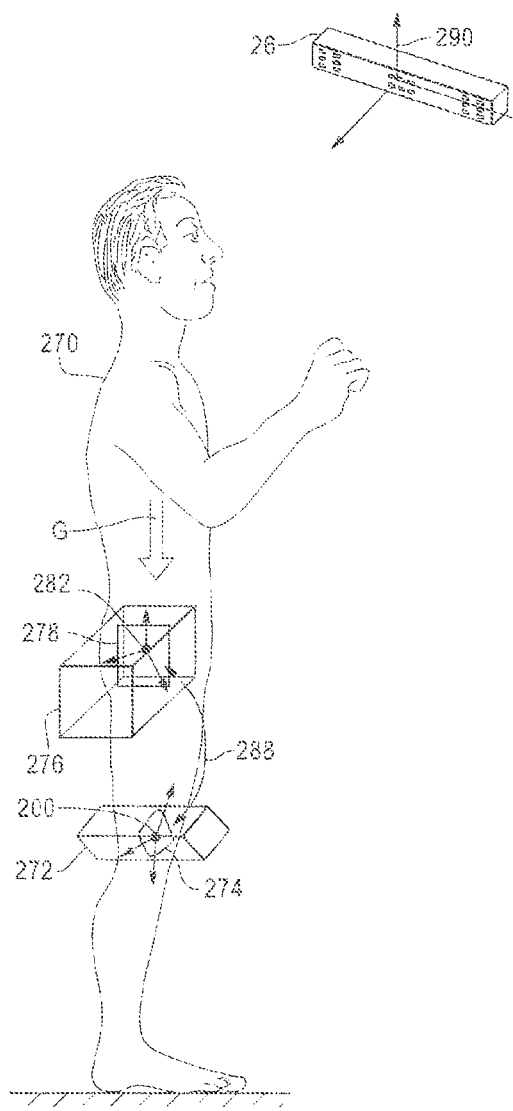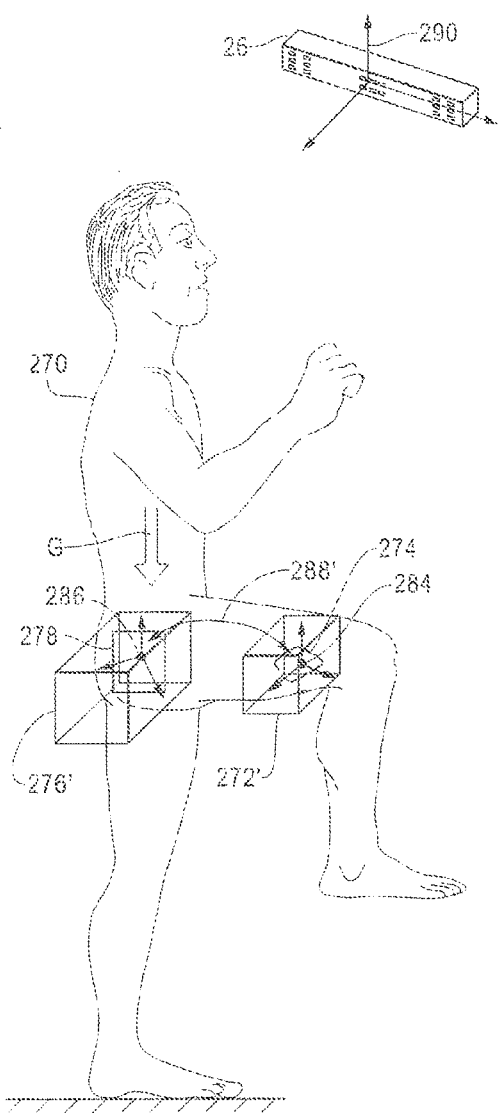

REGISTRATION OF ANATOMICAL DATA SETS

RELATED APPLICATIONS

This application is a continuation of U.S. patent application Ser. No. 12/835,384 filed on Jul. 13, 2010, the contents of which are hereby incorporated by reference in its entirety.

CROSS REFERENCE TO RELATED APPLICATIONS

—Not applicable—

REFERENCE REGARDING FEDERALLY SPONSORED RESEARCH OR DEVELOPMENT

—Not applicable—

SEQUENTIAL LISTING

—Not applicable—

BACKGROUND OF THE INVENTION

1. Field of the Invention

The present disclosure relates to systems and methods for registering anatomical image data sets and relating anatomical information between anatomical image data sets.

2. Description of the Background of the Invention

There exist various techniques in computer assisted surgical procedures to register patient related data across different modalities and/or different time frames. Such patient related data can include, for example, anatomical information or image data obtained using a variety of imaging techniques or modalities, such as ultrasound, magnetic resonance imaging ("MRI"), computed tomography ("CT"), single photon emission computed tomography, positron emission tomography, etc. One technique to register patient related data across different modalities is a "point to point" or "paired point" matching technique, wherein landmarks or fiducials that can be identified across different modalities are used to determine a transformation matrix and establish a spatial relationship between the different modalities. In one example, landmarks or fiducials are placed on a patient prior to an image scan, for example, an MRI or CT scan, and such landmarks or fiducials are identified in the image scan and on the patient during a surgical procedure to establish the registration between the patient and patient related data from the image scan.

In another technique, surface registration is used, wherein multiple surface points of a structure or region of interest are used to establish a registration surface. The surface points are identified independently in different modalities often using different techniques. In one embodiment, the surface registration technique is used in ear-nose-throat surgery where a face of a patient is used as a registration surface. For example, a CT or MRI scan of the face of the patient is obtained and the surface of the skin is identified in the scan and then matched to digitized points on the face of the patient during surgery. Such digitized points can either be collected directly with a digitization device, such as a pointer, or indirectly via a registration mask.

The above registration techniques generally serve only to register patient related data from one modality to a different modality. Most commonly, the registration techniques register pre-operative image data of a patient to the anatomy of the patient during surgery for localization purposes of surgical instruments used to perform the surgery.

In some types of procedures, such as procedures related to musculo-skeletal ailments, biomechanical and functional information of joints play an important role in determining the extent or cause of a disease. Such information is generally captured through a motion analysis. In one example of a motion analysis, fiducials are placed on the skin of a body part to be analyzed. A navigation system tracks the fiducials as the body part is moved and the movement of the fiducials is analyzed to establish a biomechanical model of the body part. An obvious downside of this technology is that the fiducials do not directly relate to the underlying bony structures and that shifts in skin or soft tissue occurs during motion. Such shifts can contribute to relatively large motion artifacts and inaccuracies in the results of the motion analysis and the established biomechanical model.

A technique that overcomes soft tissue shift is the direct implantation of fiducials, such as small tantalum beads, onto the bones of the subject, wherein the fiducials are tracked using stereo-radiography techniques during movement of the body part of the patient. Some of the obvious disadvantages of this technique are that a surgical procedure is required for bead implantation and that the motion analysis utilizes ionizing energy.

Further, during a surgical procedure, a motion analysis may not adequately capture functional information of the joints if the motion of the limb is passive. For example, when a surgeon moves the limbs of a patient, or if the patient is anesthetized and lying on an operating room table, no voluntary muscular forces are active to counter the effects of gravity on the body masses.

As surgical procedures around musculo-skeletal ailments start to shift away from pure static standing considerations to a more functional assessment of the joints and towards early intervention, the ability to capture joint related functional information and easily relate such information to the planning and execution of surgical procedures becomes increasingly important.

SUMMARY OF THE INVENTION

According to some aspects, a computer-implemented method of registering information associated with a first data set to a second data set is disclosed. The method comprise the steps of collecting a first data set of an anatomical structure with an imaging device, developing additional information for the first data set, wherein the additional information has a unique identifiable spatial relationship to the structure of the first data set, and establishing a first arbitrary reference frame for the first data set. The first reference frame is established without reference to any pre-selected landmark on the structure, and the first reference frame has a unique spatial relationship to the first data set. The method also comprises the steps of collecting a second data set of an anatomical structure with an imaging device, establishing a second arbitrary reference frame for the second data set, transforming the first reference frame to the second reference by matching a unique spatial parameter of the first data set with the same unique spatial parameter of the second data set, and registering the additional information with the second data set.

According to other aspects, a computer-implemented method of associating spatial information related to a first volume data set of an anatomical structure with a second volume data set of the anatomical structure is disclosed. The method includes the steps of obtaining a first volume data set of the anatomical structure with a computer surgical navigation system, assigning a first arbitrary reference frame to the first volume data set, calculating an inherent feature in the first volume data set, correlating the inherent feature to the first arbitrary reference frame, and associating additional spatial information with the first volume data set. The inherent feature has a unique position and orientation in relation to the anatomical structure that can be identified from any reference position, and the additional spatial information has a unique spatial relationship correlated with the first arbitrary reference frame. The method further includes the steps of obtaining a second volume data set of the anatomical structure with a computer surgical navigation system, assigning a second arbitrary reference frame to the second volume data set, identifying the inherent feature in the second volume data set, and correlating the inherent feature to the second arbitrary reference frame. The method also includes the steps of registering the first volume data set with the second volume data set based on the inherent feature, correlating the additional spatial information to the second volume data set in registration therewith, and displaying the additional spatial information in registration with the second volume data set on a display device. The registering step is performed by a computer According to additional aspects, a system for collecting and manipulating a volume data set of an anatomical structure includes means for obtaining a first volume data set of an anatomical structure of a patient and a second volume data set of the anatomical structure, and means for calculating an inherent feature of the first volume data set and the second volume data set. The inherent feature has a unique position and orientation in relation to the anatomical structure that can be identified from any reference position. The system further includes means for assigning a first arbitrary reference frame to the first volume data set and a second arbitrary reference frame to the second volume data set, means for correlating the inherent feature to the first arbitrary reference frame, and means for associating additional spatial information with the first volume data set. The additional spatial information has a unique spatial relationship correlated with the first arbitrary reference frame. The system also includes means for registering the first volume data set with the second volume data set based on the inherent feature, and means for correlating the additional spatial information to the second volume data set in registration therewith.

According to further aspects, a method of establishing a position a portion of a bone that has been altered from a normal shape includes the step of collecting a first volume data set for a first bone that is unaltered, wherein the first volume data set includes volume data for first and second portions of the first bone. The method also includes the steps of identifying a first unique spatial characteristic of the volume data for the first portion of the first bone, establishing a first arbitrary reference frame for the first volume data set correlated with the first unique spatial characteristic, and identifying a unique spatial relation between the first arbitrary reference frame and the second portion of the first bone. The method further includes the step of identifying a second bone that normally mirrors the first bone about a centerline, wherein the second bone includes a first portion and a second portion that correspond as substantially mirror structures to the first and second portions of the first bone, respectively, and wherein the second bone has been altered from a normal shape such that the first portion of the second bone is in an altered position with regard to the second portion of the second bone. The method further includes the steps of collecting a second volume data set of the first the first portion of the second bone, identifying a second unique spatial characteristic of the second volume data set, wherein the second unique spatial characteristic substantially mirrors the first unique spatial characteristic, registering in mirrored correlation the first volume data set with the second volume data by correlating the first unique spatial characteristic with the second unique spatial characteristic, and re-establishing the normal position of the second portion of the second bone to coincide with the position of the second portion of the first bone as related to the registered position of the first portion of the first bone.

Other aspects and advantages of the present invention will become apparent upon consideration of the following detailed description.

BRIEF DESCRIPTION OF THE DRAWINGS

FIGS. 2 and 2A are flowcharts of registration procedures according to the present disclosure;

FIGS. 3A, 3B, and 3C illustrate the development of additional spatial information for an anatomical structure represented by a first data set and the relation of such information to a second data set;

FIG. 5 illustrates the development of additional spatial information for a first anatomical structure and the relation of such information to a second anatomical structure that mirrors the first anatomical structure;

FIGS. 7A and 7B show an example of determining functional motion parameters of a hip of a patient.

DETAILED DESCRIPTION OF THE DRAWINGS

Systems and methods of the present disclosure may be used to register different data sets related to one or more structures of a patient and/or to relate additional information from one such data set to another such data set, wherein the additional information may not be available or practically obtainable for the other data set. In many instances, positional information of non-contiguous regions of a body is tied together without the need to identify or relate to local anatomical reference frames based on pre-defined anatomical landmarks. In one application, functional information from one data set is related to another data set to facilitate the performance of a functional assessment of a structure. For example, the structure can be an anatomical structure, such as a bone or joint of a patient, and the volume data set can be an image data set of the bone or bones obtained using an ultrasound probe or other known imaging techniques of modalities. The functional information that is developed for the anatomical structure from a pre-operative image data set can be related to an intra-operative image data set to aid in the planning and execution of surgical procedures and/or to facilitate early identification and prevention of certain diseases or harmful conditions. In another embodiment, other information can be utilized, for example, to re-establish an anatomical reference frame that is accessible in one data set but not another. A further aspect of the present disclosure is the ability to register different data sets for a structure without a need for a predefined landmark or fiducial on the structure. Instead, arbitrary reference frames are established for different data sets and used to register such data sets.

Figure 1:
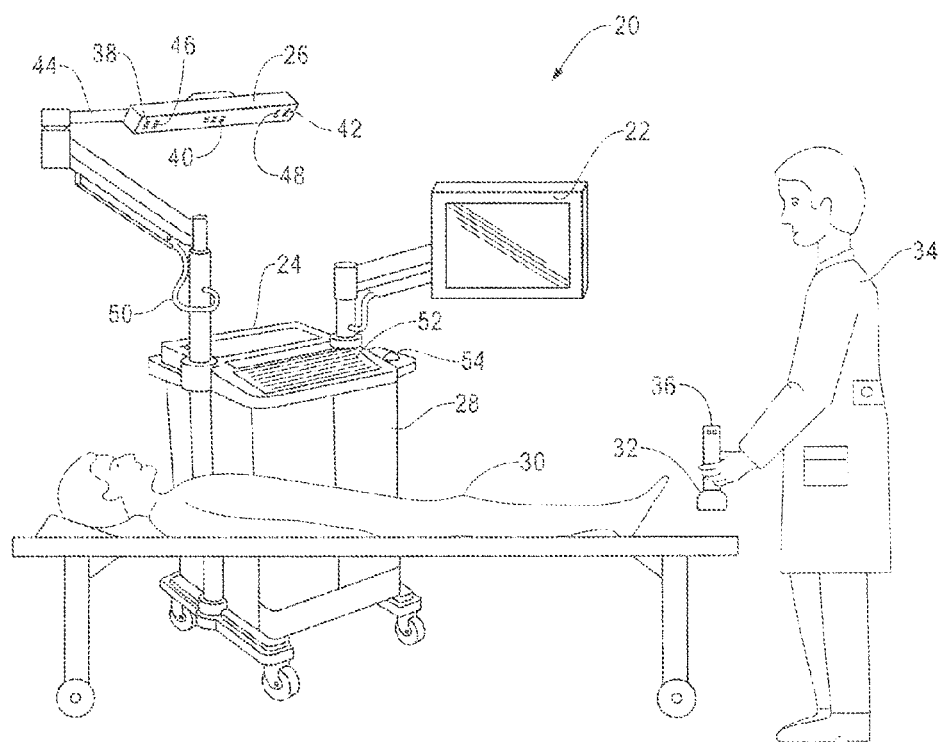
FIG. 1 is a schematic view of an embodiment of a surgical navigation system adapted to implement methods of the present disclosure.

Turning now the drawings, FIG. 1 is a schematic view of a surgical navigation system 20 that is adapted to implement the steps of the procedure(s) disclosed herein. The surgical navigation system 20 includes a display unit 22, a computer system 24, and a camera array 26. In the present embodiment, the computer system 20 is housed in a moveable cart 28. The computer system 24 may be, for example, any type of personal computer having a memory unit, a CPU, and a storage unit (all not shown), as would be apparent to one of ordinary skill in the art. The display unit 22 can be any conventional display usable with the computer system 24, such as a standard computer monitor or television. An exemplary surgical navigation system is the Stryker Navigation system available from Stryker Corporation.

The surgical navigation system 20 is adapted to receive image data of a patient 30. In one embodiment, image data is obtained by an ultrasound probe 32 manipulated by a user 34, such as a surgeon or a nurse, and transmitted wirelessly to the computer system 24. Alternatively or additionally, a system that uses wires to transmit data between the ultrasound probe 32 and the computer system 24 can be used. In the present embodiment, the ultrasound probe 32 provides a non-invasive, non-ionizing, and portable imaging modality to obtain image data of the patient 30. Further, the ultrasound probe 32 provides image data for underlying bones to overcome skin shift related motion artifacts. However, in other embodiments, image data can be collected using any other acceptable imaging technique or modality, such as magnetic resonance imaging ("MRI"), computed tomography ("CT"), single photon emission computed tomography, positron emission tomography, and the like.

The camera array 26 is adapted to detect the position of a sensor 36 coupled to the ultrasound probe 32 to track the position and orientation of such ultrasound probe 32. By way of non-limiting examples, the sensor 36 can be one or more light emitting diodes ("LEDs"), the camera array 26 can include a first camera 38, a second camera 40, and a third camera 42, and the first, second, and third cameras 38, 40, 42, respectively, can be three CCD cameras that are adapted to detect infrared ("IR") signals generated by the sensor 36. Although not shown, the user 34 can use other surgical tools and instruments that are capable of being tracked by the camera array 26 in the same manner as the ultrasound probe 32. These additional surgical tools and instruments may have sensors 36 that comprise, for example LEDs, either built into the tool or instrument or physically associated therewith in a known or determinable position and orientation sufficient for tracking the position of the instruments.

The camera array 26 is mounted on a rotatable arm 44 attached to the movable cart 28 so that the camera array 26 has a sufficient line of sight to a relevant field where a procedure is to take place. In other embodiments, the camera array 26 may be mounted onto an operating room wall (not shown) or onto another convenient surface or location.

The surgical navigation system 20 can be an active optical system that includes at least one infrared transceiver that is used to communicate data to and from the sensor 36. For example, in the present embodiment, the camera array includes a first transceiver 46 and a second transceiver 48 located apart from each other. While the present disclosure is described using an active optical surgical navigation system, the systems and methods of the present disclosure can also be used with other surgical navigation technologies and systems, such as passive optical systems, magnetic based systems, inertial navigation based systems, and the like. Other computer-assisted systems also can be used including RFID based systems, video imaging based systems, and the like.

The camera array 26 is connected via a cable 50 to a localizer (not shown) or in some instances directly to the computer system 24. The localizer cooperates with the camera array 26 to identify the location and orientation of the sensor 36 on the ultrasound probe 32 within the line of sight of the camera array 26. In one embodiment, the localizer converts raw position data of the LEDs into the orientation of individual LEDs of a plurality of LEDs that make up the sensor 36 and transmits this information to the computer system 24. In another embodiment, the localizer converts raw position data of the LEDs into the position and orientation of the ultrasound probe 32 and transmits this information to the computer system 24. In a further embodiment, a software program executed by the computer system 24 can convert the raw data into the orientation of the ultrasound probe 32. The conversion of the raw position data is well known to one skilled in the art. The computer system 24 may optionally be controlled remotely by control buttons (not visible) located on the ultrasound probe 32 or otherwise easily accessible to the user 34. The computer system 24 also includes one or more input devices, such as a keyboard 52, a mouse 54, or any other input devices for operating the computer system 24.

Referring next to FIGS. 2 and 2A, methods of registering a first volume data set of an anatomical structure to a second volume data set of the anatomical structure is disclosed. The methods are preferably performed using a computer surgical navigation system as disclosed herein, wherein the navigation system can track the position of one or more gathering devices for gathering the volume data sets, storing position data and extracting information therefrom, and correlating the position data with the volume data sets.

FIG. 2 describes a broad view of a method of registration, in which control initiates at a block 80 that collects a first data set for a structure, such as an anatomical structure of a patient. Following the block 80, control passes to a block 82 that develops additional positional information related to the first data set, and a block 84 that determines or establishes a first reference frame for the first data set. The first reference frame is preferably an arbitrary reference frame. A block 86 collects a second data set, a block 88 determines a second reference frame for the volume second data set. Thereafter, control passes to a block 90 that transforms the first reference frame into the second reference frame, and a block 92 relates the additional spatial information from the first reference frame, such as functional information for the anatomical structure, to the second reference frame.

FIG. 2A describes a more detailed view of a method embodying the method of FIG. 2, wherein control initiates a block 100 that collects a first data set for a structure, such as an anatomical structure of a patient. The first data set can include a first volume data set for the anatomical structure. As used herein, the term anatomical structure can include an entire anatomical structural unit, such as a complete bone, and the term anatomical structure can include a smaller portion of the entire anatomical structural unit less than the entirety, such as just a small portion of the bone. Preferably, the volume data set includes information about the position and orientation of the anatomical structure, such as a bone or a joint. The first volume data set is collected using a subcutaneous imaging device, such as the tracked ultrasound probe 32 of FIG. 1, wherein the volume data set includes an image of a bone or other subcutaneous structure on a patient. Other image capturing devices and modalities for capturing the first image data set may be used also, such as CT scan, MRI, X-rays, etc. The first volume data set may be obtained pre-operatively, for example. The first volume data set preferably includes image data regarding the anatomical structure, and may include two-dimensional (2D) image data and/or three-dimensional (3D) image data. One exemplary capturing device and modality for capturing the first image data set includes a 2D or 3D ultrasound imaging device, if a 2D ultrasound probe is used, such probe can be used to collect volume data by collecting multiple slices of a region that includes the anatomical structure. The position of the capturing device is tracked by the surgical navigation system while capturing the volume data set. Preferably, the anatomical structure is in a fixed position while the volume data set is captured, which dispenses with a need to track the position of the anatomical structure separately during the capturing. The anatomical structure optionally may be tracked during the capturing, in which case the anatomical structure may move during the capturing and/or additional robustness may be incorporated into position data for the acquired volume data set encompassing the anatomical structure.

After block 100, control passes to a block 102 that assigns or determines a first reference frame for the first data set. The first reference frame is preferably an arbitrary reference frame established without reference to any pre-defined landmark, such as a fiducial or particular anatomical landmark, on the anatomical structure. For example, the first reference frame can be of a camera assembly, an ultrasound probe, or the first volume data set itself, such as, a center of the first volume data set. Other ways to establish the arbitrary reference frame to distinguish from other types of reference frames can also be used. The reference frames may be established by any known or commonly used image processing algorithms. Once established, the arbitrary reference frame preferably has a unique spatial relationship to the volume of the subject anatomical structure, such as a bone, and the arbitrary reference frame remains fixed in the same position relative thereto.

Control passes to a block 104 that identifies an inherent feature of the first volume data set, such as a spatially unique physical spatial aspect of the volume data set. Preferably, the inherent feature has a unique position and orientation in relation to the anatomical structure that can be identified from any reference position. In a preferred method, the computer system 24 is adapted with appropriate command routines to calculate an image moment of inertia of the volume data set, which is constant with regard to the volume regardless of what point of view the volume is acquired or viewed from. Using the moment of inertia can be advantageous because any given volume has a constant moment of inertia that has a unique fixed spatial relation to a data set representing a particular volume and regardless of the point of view from which the volume is viewed. Therefore, for example, the moment of inertia of a volume data set of a particular portion of a bone will be in the same relative position to that portion of the bone regardless of from what position or point of view the volume data set is obtained. Other methods of determining a spatially unique physical spatial aspect of the volume data set may be used and may obtain alternative or additional uniquely defined spatial information about the anatomical structure, such as surface contour information, point landmarks, etc., that could be used to define the arbitrary reference frame.

Thereafter, control passes to a block 106 that correlates the first arbitrary reference frame to the spatially unique physical aspect of the volume data set. In one example, the block 88 correlates the first arbitrary reference frame and the image moment of inertia by a known unique spatial relationship therebetween, such as the xyz Cartesian coordinates of the image moment of inertia within the first arbitrary reference frame. In one exemplary method, the first arbitrary reference frame is assigned such that the moment of inertia defines an axis of the arbitrary reference frame. Other alternative and/or equivalent methods or systems for correlating the arbitrary reference frame to the spatially unique physical aspect may be used.

Control passes to a block 108 that develops and/or associates additional positional information with the first volume data set, wherein the additional spatial information has a unique spatial orientation relative to the first arbitrary reference frame. The additional positional information can include functional information for the anatomical structure, such as a gravity vector that acts on the anatomical structure and/or orientations of parts of the anatomical structure with respect to each other. In one embodiment, the first data set is a pre-operative volume data set and the functional information is obtained for the anatomical structure when a patient is in a generally standing or upright position. In other embodiments, the functional information can be obtained by other methods, as would be apparent to those skilled in the art.

The additional spatial information may be contiguous with the first volume data set. For example, the additional spatial information may include gravity vector information that defines a gravity vector through the first volume data set at the time the volume data set was obtained. The gravity vector may be obtained by any known method. One such method includes having a gravity sensing device, such as an accelerometer, installed on the camera of the surgical navigation system, wherein the gravity sensing device identifies the local gravity vector while the first volume data set is being gathered. The gravity vector information is then associated with the volume data set such that the gravity vector can be uniquely located with respect to the first arbitrary reference frame.

In another example, the additional spatial information set may be non-contiguous to the first volume data set. For example, the additional spatial information may include a vector that identifies the location and orientation of another reference frame. The other reference frame may be another arbitrary reference frame for a non-contiguous volume data set that does not overlap with the first volume data set, wherein the non-contiguous volume data set relates to another anatomical structure or another portion of the same anatomical structure. In one instance, the first volume data set may be of a first portion of a bone and the non-contiguous volume data set may be of a second portion of the same bone. The other reference frame may also include a global reference frame that is common to several volume data sets, such as a camera reference frame of a camera of the surgical navigation system. In this manner, the specific locations and/or orientations of reference frames of each of one or more non-contiguous volume data sets may be interlinked with the first volume data set such that the location and orientation of any one or more of the volume data sets may be used to identify the location and orientation of one or more of the other non-contiguous volume data sets even though the volume data sets are not specifically overlapping and not presently viewed.

Other types of additional spatial information that may have unique spatial characteristics in relation to the anatomical structure represented by the volume data set may also be identified with the volume data set. By way of non-limiting examples, other types of additional spatial information could include location and orientation vector(s) of the arbitrary reference frame of the volume data set with respect to other local anatomical reference frames of the patient, such as a pelvic plane, femoral mechanical axis, femoral anatomical axis, and other relevant local reference points and/or frame such as commonly used in the art. However, the disclosure contemplates that any type of spatial information that has a unique identifiable spatial characteristic in relation to the anatomical structure represented by the volume data set may be associated with the volume data set as considered necessary or expedient for various and different specific applications.

Control passes to a block 110 that collects a second data set. In one example, the second volume data set may be of the same anatomical structure as for the first volume data set or at least have significant overlap therewith. There is sufficient overlap between the first data set and the second data set so that the first and second data sets can be registered in a subsequent step described hereinafter. In a preferred embodiment, there is at least about a seventy percent overlap of the anatomical structure captured in the first volume data set and the anatomical structure captured in the second volume data set. More than seventy percent overlap may be even more preferable in some instances, and less than seventy percent overlap may be sufficient in other instances. The second volume data set may be obtained from a same point of view as the first volume data set or it may be obtained from a different point of view.

In another example, the second volume data set may be of a different anatomical structure that has some known or determinable spatial relationship to the first anatomical structure. In one aspect, the first volume data set may be of a bone or portion thereof on one side of a patient's body and the second volume data may be of a bone or portion thereof on the opposite side of the patient's body that corresponds as a substantially mirror image of the first bone. By way non-limiting example, the first volume data set may include image data of a left femoral head and the second volume data set may include image data of a right femoral head. The left femoral head is assumed to be mathematically equivalent to a mirror image of the right femoral head in relation to a centerline of the body. In this manner, the left femoral head and the right femoral head have a known or determinable spatial relationship to each other about the centerline of the body. For example, a prominent standard anatomical feature of the femoral head, such as the lesser trochanter, may be identified as a landmark that is assumed to be in the same location on each of the left and right femurs but in mirror image relationship to each other about a centerline of the body. Other identifiable relationships between different anatomical structures can also be identified and used in a similar manner as described herein.

In some applications, the second volume data set is obtained during a different portion of a procedure than the first volume data set, such as intra-operatively. In one example, the second data set is an intra-operative volume data set of the same bone or portion thereof that is obtained while the patient is anesthetized and lying on an operating table. In other applications, the first and second volume data sets could be collected during the same portion of a surgical procedure, such as both being collected intra-operatively or both being collected pre-operatively. Additionally, one or more volume data sets may be collected post-operatively, such as to aid in post-operative diagnostics, for example.

The second data set can be collected using the same modality or a different modality than the first data set. In one example, both the first and second volume data sets are obtained using a 3D ultrasound imaging system having a tracking device attached thereto for being tracked by the surgical navigation system. In the present example, the second data set is also collected using the ultrasound probe 32 tracked by the surgical navigation system 20.

Thereafter, control passes to a block 112 that assigns a second reference frame to the second volume second data set. Like the first reference frame, the second reference frame can be an arbitrary reference frame and can be assigned or determined in a similar manner as described herein. The second arbitrary reference frame preferably is defined uniquely by the second volume data set. In one example, the second arbitrary reference frame is defined by the anatomical structure in the same manner as described previously herein with respect to the first anatomical structure. The second reference frame can be the same as or different from the first reference frame.

Control also passes to a block 114 that identifies an inherent feature of the second volume data set, such as a spatially unique physical spatial aspect of the volume data set. Where the first and second volume data sets are of substantially the same anatomical feature, the inherent feature of both volume data sets is preferably the same because the same anatomical feature would have the same unique spatial aspect, such as the image moment of inertia, for both the first and second volume data sets. For example, in a system that calculates an image moment of inertia of an ultrasound image, the moment of inertia of the structure is constant and substantially unique relative to a given structure regardless of the point of view from which the structure is viewed. Therefore, the moment of inertia of the same anatomical feature is uniquely identifiable in different volume data sets of the anatomical feature taken from different points of view. In such an example, the second arbitrary reference frame may also be uniquely spatially associated with the image moment of inertia.

A block 116 correlates the second reference frame to the inherent feature of the second volume data set in the same manner as in block 106 or any sufficient manner.

Control then passes to a block 118 that registers the first reference frame into the second reference frame. In one embodiment, the block 118 performs data set matching, such as by finding the unique moment of inertia of each image and correlating the first and second arbitrary reference frames to each other based on matching the moment of inertia of the first volume data set to the moment of inertia of the second volume data set and calculating an appropriate transformation matrix therefrom. Another possible method of data set matching may include conducting a different volume data match of the first and second volume data sets, whereby first and second volume data sets are virtually overlaid and correlated to each other using any suitable or commonly known method. The registration may also be performed using other methods, such as volume-volume matching, surface-surface matching, and/or point-to-point matching. Under any registration technique, a mathematical transformation including rotation, translation, and scale, is calculated preferably by the computer system 24 that will register a common or assumed common spatially unique feature in the two volume data sets. The computer system 24 then transforms one or both of the arbitrary reference frames to bring the spatially unique feature, and thus the volume data sets, into registration with each other. Other equally efficacious methods of calculating and performing a suitable transformation and registration may be used as would be known to a person skilled in the art.

Control then passes to a block 120 that relates the additional spatial information from the first reference frame, such as functional information for the anatomical structure, to the second reference frame. The additional spatial information from the first volume data set is related to the second arbitrary reference frame of the second volume data set after (or contemporaneously as) the first and second volume data sets have been brought into registration. In this manner, the additional spatial information is associated with the second arbitrary reference frame in correct registration therewith even though the additional spatial information is not directly available when the second volume data set is acquired. For example, when the additional spatial information includes the gravity vector as described above, the gravity vector is associated with and brought into registration with the second volume data set in proper orientation to the anatomical structure even when the anatomical structure is in a different orientation. When the additional spatial information includes a vector that identifies the location and orientation of another reference frame as described above, the location and orientation of the non-contiguous volume data sets not part of the second volume data set may be identified based on the association and registration of the vector information comprising the additional spatial information.

Optionally, control may then pass to a block 122 that displays in registration with the second volume data set on a display device. Additional manipulations and uses of the additional spatial information may also be performed as desired.

The blocks 100-122 described above can be rearranged, reordered, or modified by combining to include fewer or breaking down further additional steps, as would be apparent to one of skill in the art. As shown in FIG. 2A, the steps 100-122 in some instances correlate with the steps 80-92 shown in FIG. 2, such as by being considered sub-steps thereof. Further, the logic represented by the flowcharts of FIGS. 2 and 2A can be implemented by any computer system that is adapted to implement the blocks 80-92 and/or 100-122, such as the surgical navigation system 20 of FIG. 1. In one embodiment, the computer system 24 includes appropriately programmed software and hardware to perform the blocks and processes of FIGS. 2 and 2A.

Figure 3A:
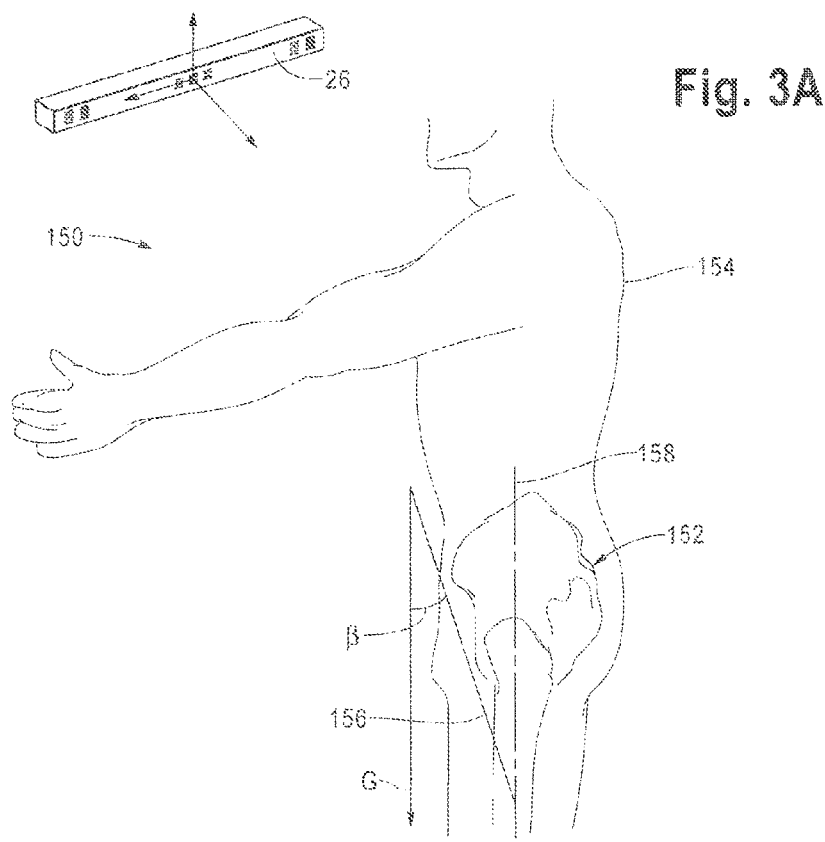
Figure 3B:
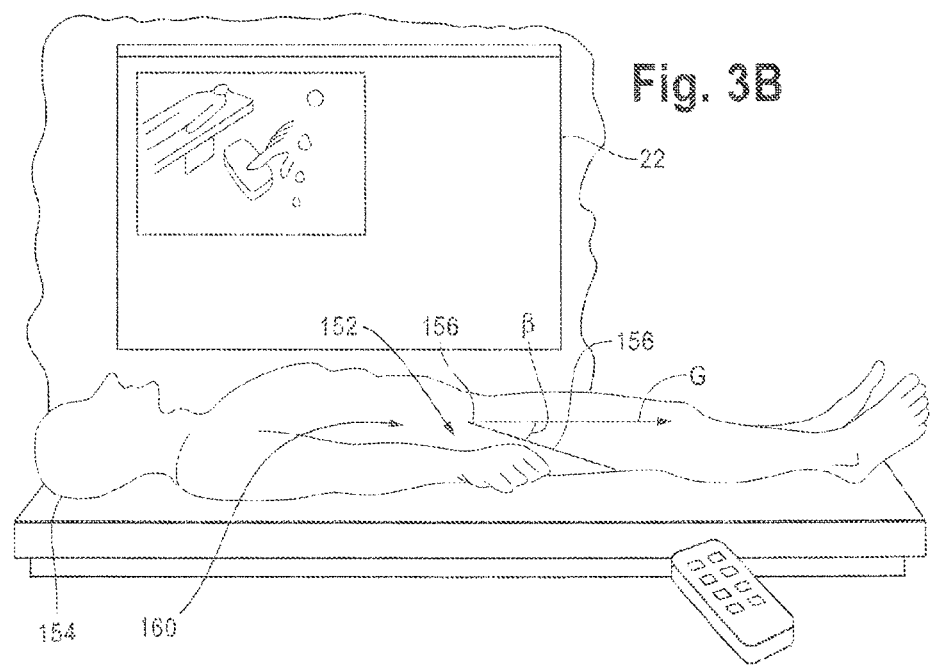

FIGS. 3A, 3B, and 3C illustrate an example where the additional spatial information includes functional information for an anatomical structure that is obtained from a pre-operative volume data set and related to an intra-operative volume data set so that the functional information can be used during a surgical procedure on a patient. In one such surgical procedure, for example a hip joint arthroplasty procedure, a gravity vector that acts on the various bones that make up the hip joint can be an important factor for the precise positioning of components of a prosthetic hip implant based on certain functional motion characteristics of the patient. In other embodiments, functional information may be obtained for the anatomical structure in a plurality of different positions or over a period of time. For example, functional information can be obtained for a knee joint in various positions to collect extension/flexion, varus/valgus, and other information for use during a surgical procedure.

In a joint arthroplasty procedure, a prosthetic component is placed accurately and effectively using the arbitrary reference frames discussed herein instead of relying on local biomechanical/anatomical references, such as a femur mechanical axis, pelvic frontal plane, or other standard local anatomical reference frames. As used herein, a "local" reference frame is a reference frame based on specific accepted or pre-defined defined anatomical features of a patient, such as specific skeletal landmarks. In contrast, an "arbitrary reference frame" refers to a reference frame that is identified uniquely based solely on the feature being looked at, such as the specific volume data set being viewed. Thus, the arbitrary reference frame is not dependent on locations of one or more specific pre-defined anatomical landmarks with respect to other portions of the anatomy but is correlated to and identifiable from unique spatial characteristics of only the anatomy of interest.

Relating the functional information, such as the gravity vector G, to the intra-operative procedure facilitates placement of correct prosthetic components in an optimal position and alignment based on the natural motion and movement patterns of the patient. The position and alignment of the prosthetic can further be optimized using a plurality of parameters that include, for example, joint specific anatomical and kinematic constraints, patient life-style specific activities, and prosthetic design specific geometrical and kinematic constrains. Still further optimization can be realized through incorporation of other relevant factors that arise or become visible intra-operatively, such as after the preparation of a joint surface to accept a prosthetic component.

FIG. 3C illustrates steps in one method and specific example that utilizes additional spatial information on a computer implemented surgical navigation system, such as the surgical navigation system 20, including functional information relative to that shown in FIGS. 3A and 3B. A block 170 acquires a pre-operative image volume data set 150 of a hip 152 or of parts of the hip of a patient 154 while the patient is standing. Preferably, the image volume data set 150 is acquired using the ultrasound probe 32 while being tracked by the camera array 26 to gather image data of the bones of interest in the hip joint, and the image data is stored in a suitable electronic memory available to the surgical navigation system.

A block 172 defines an arbitrary axis, such as an axis of the camera array, to the image volume data set 150, identifies a unique spatial parameter of the image volume data set, and correlates the arbitrary axis to the spatial parameter. In this particular example, the unique spatial parameter preferably includes the image moment of inertia of the image volume data set of the hip bones, calculated as discussed previously herein. The arbitrary axis is optionally also correlated to a local anatomical parameter of the hip 152, such as a frontal plane 156 of the hip 152 as shown in FIG. 3.

A block 174 assigns additional spatial information including functional information, such as a gravity vector G, to the image volume data set 150. In this example, the gravity vector G is shown pointing downwards to the floor in relation to the hip 152 in FIG. 3A because the patient is standing upright while the image volume data set 150 is obtained. The gravity vector is acquired using an inertial system with an accelerometer, but can be acquired by any sufficient system known in the arts, such as a liquid level measurement system or other systems. The gravity vector G is spatially assigned by determining an orientation of the gravity vector G with respect to the anatomical parameter and/or arbitrary axis, such as a specific tilt angle $\beta$ with respect to the frontal plane 156. In further examples, other anatomical parameters can be defined, for example, a functional plane 158, an iliac crest, a pubic symphysis, and the like, and various planes and angles defined thereby, wherein the gravity vector G can be related to such anatomical parameters.

A block 176 collects an intra-operative image volume data set 160 of the same general area while the patient 154 is lying in a generally prone position in a similar manner as with the block 170.

A block 178 performs a data match to register the pre-operative image volume data set 150 and the intra-operative image volume data set 160 using any suitable data matching technique, such as image inertia matching or the volume data matching techniques discussed previously. Due to such registration, the gravity vector G is simultaneously or subsequently transferred to the intra-operative volume data set 160 for use during the procedure.

A block 180 displays the image volume data set 160 on the display unit 22 with the gravity vector G shown in registration with the bones of the hip. A replacement prosthesis can then be aligned with the bones of the hip using the surgical navigation system 20 so as to have a relationship to the bones that has been preselected based on the position of the bones with respect to the gravity vector G.

The method shown and described in relation to FIGS. 3A-3C is preferably implemented on the surgical navigation system 20, and blocks 172, 174, 178, and 180 are preferably performed by appropriate computer software routines associated with and preferably controlling the computer system 24 in any available manner known to one skilled in the art.

Figure 4A:
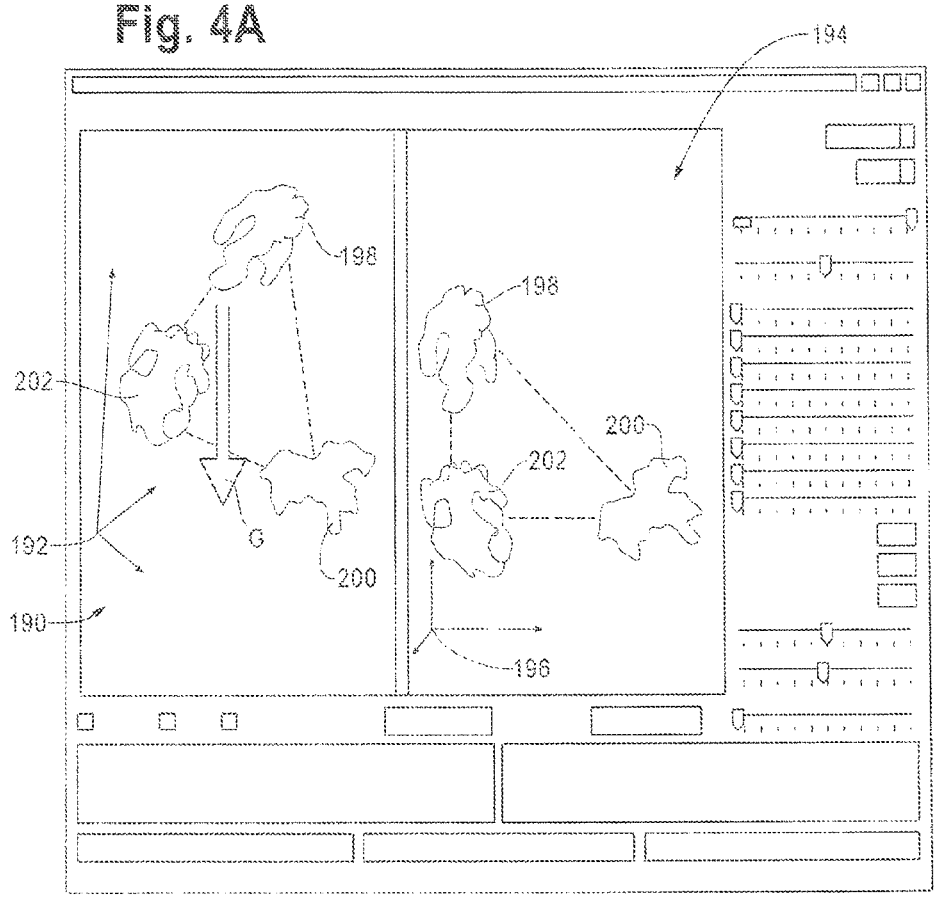
FIG. 4A, is an example screen shot
Figure 4B:
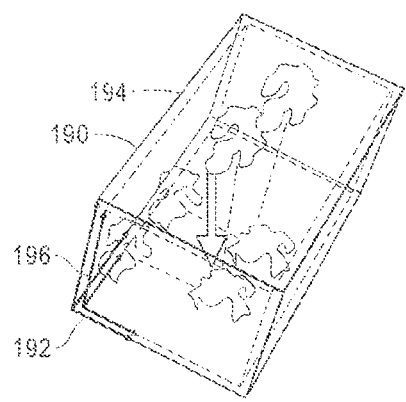
FIGS. 4B and 4C are visual representations that depict data set collection and registration.
Figure 4C:
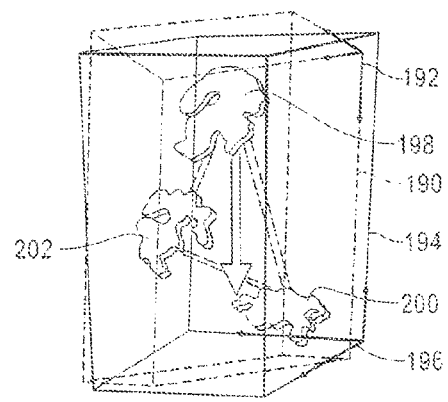

FIGS. 4A-4C illustrate an example of a volume data match registration procedure, wherein three data set collection screen shots are shown. In a first step, a pre-operative volume data set 190 of a hip of a patient is collected by an ultrasound probe and shown on a display screen as shown in FIG. 4A, and a first arbitrary reference frame 192 is assigned thereto. Optionally, additional spatial information, such as a gravity vector G, is associated in a unique spatial location with respect to the volume data set 190. An intra-operative volume data set 194 of the hip is then collected, and a second arbitrary reference 196 frame is assigned thereto. In the present example, the anatomical parameter of the hip includes a right iliac crest 198, a left iliac crest 200, and a pubic symphysis 202 in the pre-operative volume data set. The same right and left iliac crests and pubic symphysis are also identified in the intra-operative volume data set 194, wherein such structures in the pre-operative and intra-operative volume data sets can establish a unique arbitrary reference frame for the data sets. Additionally or alternatively, the image moment of inertia is calculated for each of the pre-operative and intra-operative volume data sets 190, 194 such that the image moment of inertia of the pre-operative volume data set 190 is identical or sufficiently close to the same as the image moment of inertia of the intra-operative volume data set 194. Preferably, there is about seventy percent or more overlap between the two volume data sets 190, 194. FIG. 4B shows the pre-operative volume data set 190 and the intra-operative volume data set 194 of the hip overlapping before registration, such as with the first and second arbitrary reference frames 192, 196 aligned and without being registered. The pre-operative data set 190 and intra-operative data set 194 are then registered by a reference frame transfer by overlaying and correlating the reference frames of the respective data sets, as illustrated, for example, in FIG. 4C, which shows the pre-operative and intra-operative volume data sets 190, 194 of the hip overlapping after registration. Once the pre-operative and intra-operative volume data sets are registered, the transformation between the data sets is used to relate the additional spatial information, such as the gravity vector, from the pre-operative volume data set 190 to the intra-operative volume data set 194. As discussed above, the gravity vector G is determined with respect to an anatomical parameter of the hip in the pre-operative volume data set and assigned to the volume data set in unique spatial orientation thereto.

The embodiments of FIGS. 3A-3C, and 4A-4C provide an improvement over prior surgical procedures, which typically used the functional plane 158 as an approximation for the gravity vector G. The functional plane 158 can be determined using known methods, for example, by determining an anterior superior iliac spine and by integration of a longitudinal body axes. While the functional plane 158 has provided a rather good approximation of the gravity vector, there is generally a difference of about 5° to about 10° between the orientation of the functional plane 158 and the gravity vector G. Therefore, detecting and assigning the gravity vector G is a much more accurate and reliable method for considering functional aspects of the patient during normal activity and movement parameters.

The concepts disclosed herein can also be utilized during orthopedic, reconstructive, or trauma surgery procedures, during which procedures it is important to re-establish function and anatomy of an affected area. In some cases, an unaffected area is used to mirror an affected area to provide symmetrical biomechanical parameters, such as spatial relationships, angles, and biomechanical parameters, to repair the affected area. By way of illustration only with reference to FIG. 5, in the case of a patient with a broken left femur, image data and functional information can be obtained for a healthy right femur of the patient. The functional information for the right femur can be related to the broken left femur using the procedure of FIG. 2 to provide symmetrical biomechanical parameters to repair the broken left femur. In this example, data sets for both the right and left femurs normally are obtained intra-operatively due to the circumstances of typical trauma surgery, as would be apparent to one of ordinary skill in the art.

Referring to the example of FIG. 5, a diagrammatic image data set 210 of a left femur 212 and a right femur 214 shows that the left femur 212 has suffered some trauma, such as a severe fracture 216 across the femur neck and separating the left femur head 218, while the right femur 214 is unaffected. The image data set 210 can be obtained all at once by any suitable modality, such as with the ultrasound probe 32 and the surgical navigation system 20 as described earlier, and stored on the computer system 24. The computer system 24 then develops information for the left and right femurs 212, 214 from the image data set 210. The information includes a first volume data set 220 including the left femur head 218 and a second volume data set 222 including a part of the left femur body 224. The volume data sets 220 and 222 are preferably not contiguous to each other and/or are mathematically isolated from each other on opposite sides of the fracture 216. Further, the information also includes a third volume data set 226 including the unaffected right femur 214. The third volume data set 226 includes a volume data set 228 of the head of the right femur 214 and a noncontiguous volume data set 230 of a part of the right femur body. The right femur 214 is preferably held immobile while the entirety of the volume data set 226, including the volume data sets 228 and 230, is obtained. Alternatively, a tracking device (not shown) may be attached to the femur 214 while the volume data set 226 is obtained in order to provide additional robustness to the position information of the volume data sets 228 and 230 relative to each other and/or correct for movement of the right femur while the volume data set 226 is obtained.

Each volume data set 220, 222, 228, and 230 is assigned an arbitrary reference frame, 232, 234, 236, and 238, respectively. Each reference frame 232, 234, 236, and 238 preferably has a location and orientation that is correlated to a uniquely identifiable aspect of the volume data set, such as the image moment of inertia described herein.

Additional spatial information comprising a vector 240 that uniquely defines the spatial relation, including position and orientation, of the volume data sets 222 and 230 to each other is established. Thus, the reference frames 236 and 238 are spatially correlated with each other in a global reference frame 242, such as of the camera array 26, by the vector 240 even though the two volume data sets are not contiguous with each other. Of course, other global reference frames may also be used. Calculation of the additional vector 240 may not be necessary or may be used to provide additional mathematical robustness by providing redundant measurements in an example where the volume data set 228 is contiguous with the volume data set 230.

Next, the first volume data set 220 and the second volume data set 222 of the affected left femur 212 are matched and registered with corresponding portions 228 and 230, respectively, of the third volume data set 226 of the unaffected right femur 214 in order to determine a reconstructed position of the left femur head 218 and left femur body 224 that will match corresponding portions of the unaffected right femur 214. In one exemplary method, the registration processes includes performing a reference frame transfer from the reference frame of the unaffected right femur 214 to the reference frame of both volumes 220 and 222 of the affected left femur 212. To do this, it is assumed that the shape and position of the left femur 212 should be identical and a mirror image of the shape and position of the right femur 214 about a centerline therebetween. It is also assumed that the shapes of portions of the right femur 214 captured in the volume data sets 228 and 230 correspond substantially to the shapes of corresponding portions of the left femur 212 captured in the respective volume data sets 220 and 222. With these assumptions, the reference frames 236 and 238 and corresponding volume data sets 228 and 230 and the vector 240 of the right femur 214 are mathematically mirrored about a centerline 244 to be in position to match the left femur 212. One of the volume data sets 220 or 222 of the left femur 212 is then matched to with the corresponding mirrored volume data set 228 or 230 of the right femur 214. For example, the volume data sets 222 and 238 may both include an easily identifiable three-dimensional feature, such as the lesser trochanter 246, which can be used to register the volume data set 222 with the mirrored volume data set 238. In another example, an image moment of inertia is calculated for both volume data sets 222 and 238, and the image moment of inertias are then matched after mirroring the right femur information. Other methods of registering mirrored corresponding volume data sets may also be used.

After the volume data set 222 is registered with the mirrored volume data set 238, information about the orientation of the other parts of the unaffected right femur 214 can be related to the affected left femur 212 and used by a surgeon to position properly the broken parts of the affected left femur 212. For example, the mirrored vector 240' and volume data set 228 define the theoretically correct position of the left femur head 218 in relation to the left femur body 224. Preferably, tracking devices 246 and 248 are attached to each of the left femur body 224 and the left femur head 218 and independently tracked by the surgical navigation system 20 during the entire procedure. A surgeon is then able to adjust the pieces 218 and 224 of the left femur to align with the theoretically derived locations based on the registration to the mirrored volume data sets 228, 230 of the right femur 214.

Because only the relative position of portions of an unaffected bone with respect to the corresponding portions of an affected bone are of interest, there is no need to calculate the absolute positions of the volume data sets 220, 222, 226, 228, and 230 relative to the rest of the body of the patient by using local reference frames. Rather, the volume data sets and attendant reference frames can be chosen arbitrarily. Therefore, time and computing resources are saved because there is no need to establish a local reference frame. Of course, the method is not limited to work done on a femur as describe here, but can be used with minor modifications for any anatomical structure that is substantially mirrored on opposite sides of a centerline of a body, such as arms, ribs, feet, hands, hip, etc.

Figure 6A:
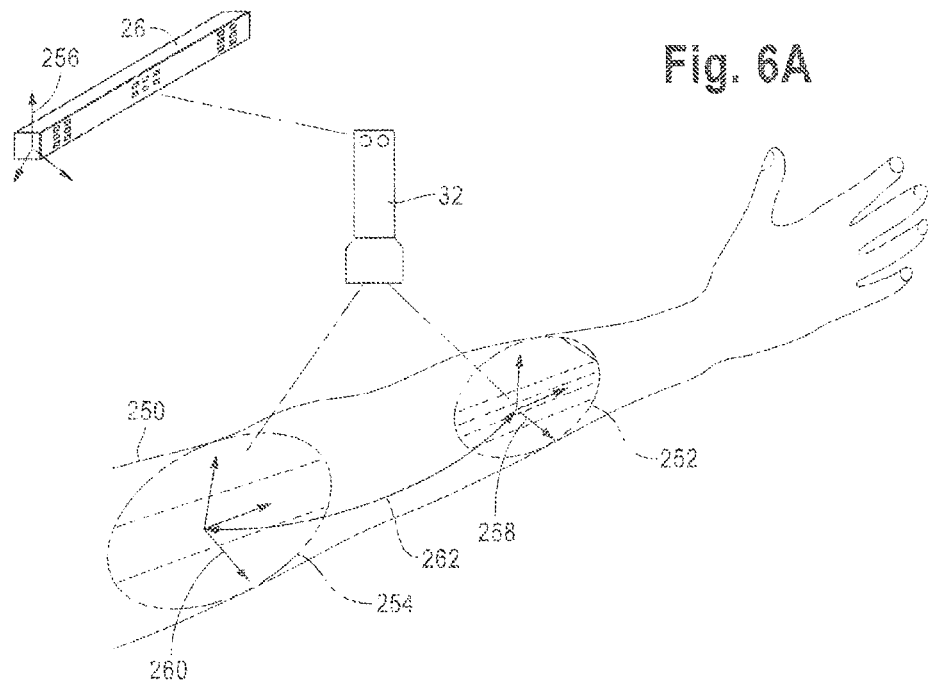
FIGS. 6A and 6B show an example of an anatomical reference frame defined pre-operatively that is not accessible during a surgical procedure.
Figure 6B:
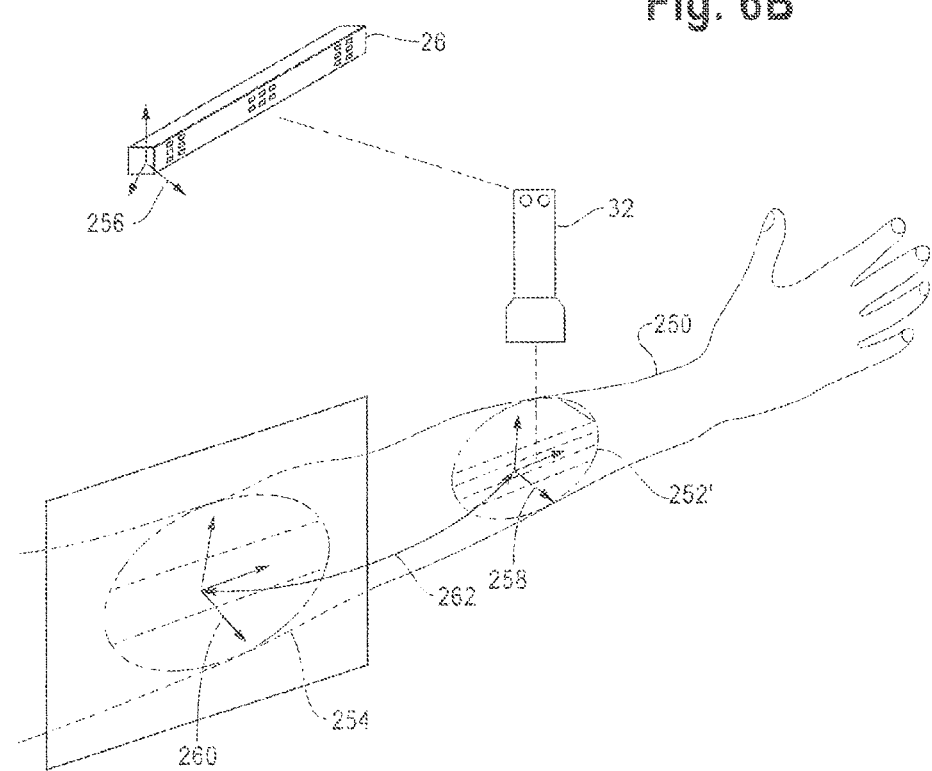

The present disclosure also contemplates the relation of spatial information from one data set relating to an anatomical structure at a first time to another data set of the same anatomical structure at another time, such as an anatomical reference frame. An exemplary situation shown in FIGS. 6A and 6B is the ability to define an anatomical reference frame pre-operatively that is not accessible during a surgical procedure due to the positioning and draping of the patient on a surgical table. In this example, a pre-operative volume data set of a forearm 250, including image data of the underlying bone(s), is collected using the tracked ultrasound probe 32 and surgical navigation system 20 at a stage when the forearm is accessible. For example, a first volume data set 252 at one location of the forearm 250 is obtained and a second volume data set 254 at another location of the forearm 250 is obtained when both locations are accessible, as shown in FIG. 6A. The pre-operative data set preferably includes regions of the forearm 250 that will be accessible after the area of interest has been prepared and draped or will otherwise be inaccessible. An anatomical reference frame or other spatial information, such as a global reference frame 256 of the camera assembly 26, is defined at a stage when the anatomy is accessible, and arbitrary reference frames 258 and 260 are defined for volume data sets 252 and 254, respectively. Each reference frame 258, 260 is uniquely identifiable from the associated volume data set, such as by having a known relation to the image moment of inertia the respective volume data set 252, 254 as discussed previously. Once defined, the anatomical reference frame or other global reference frame 256 is geometrically associated with the arbitrary reference frames 258, 260 for the pre-operative data set, and a vector 262 is determined that associates the arbitrary reference frames 258 and 260 and the respective volume data sets 252 and 254 in a unique spatial position relative to each other. During a subsequent surgery, the portion of the forearm 250 corresponding to volume data set 254 may not be accessible to the ultra sound probe 32, such as due to draping as shown in FIG. 6B, or any other reason. In such case, a subsequent volume data set 252' having substantial overlap with the volume data set 252 is collected using the ultrasound probe 32 and surgical navigation system 20, and the arbitrary reference frame 258 is re-established to relate the anatomical or global reference frame 256 to the subsequent volume data set 252'. The arbitrary reference frame 258 can be re-established in any sufficient manner, such as by matching the image moment of inertia of the volume data sets 252 and 252' in a substantially similar manner as described previously herein, by other volume matching or surface matching methods, etc. The computer system 24 re-establishes the location of the second volume data set 254 based on the vector 262 using appropriate program routines even though that area of the forearm 250 is not accessible. In this manner, the surgical navigation system 20 is able to re-establish the locations of portions of the bones of the forearm 250 based on being able to view just one volume portion of the bone that was previously identified without having to either view the other volume portions that were previously identified or define local anatomical landmarks as discussed above. The example provided herein may be applied similarly to any anatomical feature that maintains a relatively stable structural geometry over time, such as any bone, and may be extended to apply to any number of spatially inter-connectable volume data sets.

In another application, functional information about an anatomical structure is developed by collecting a plurality of volume data sets of the same anatomical structure in a plurality of different positions at corresponding different times without the need to identify a local anatomical reference frame. One example of this application is shown in FIGS. 7A and 7B, wherein functional motion parameters of a hip of a patient 270 are determined. In this example, a first volume data set 272 is gathered of a portion 274 of the patient's femur, and a first volume set 276 is gathered of a portion 278 of the pelvis, both with the patient's leg in an extended position. A second volume data set 272' is gathered of substantially the same portion of the patient's femur 274, and a second volume data set 276' is gathered of substantially the same portion 278 of the patient's pelvis, both with the patient's leg in a flexed position. Each volume data set 272, 276, 272', and 276' is assigned an arbitrary reference frame 280, 282, 284, and 286, respectively, that is correlated to a known position in relation to a uniquely identifiable feature of the respective volume data set. Preferably, each arbitrary reference frame 280, 282, 284, and 286 is correlated to an image moment of inertia of each volume data set 272, 276, 272', and 276', although other identifiable unique attributes of a particular volume data set could be used, as discussed herein. Additional positional information including a vector 288 between the volume data sets 272 and 276 and a vector 288' between the volume data sets 272' and 276' are calculated based on relation of the volume data sets to a global reference frame 290, such as a reference frame of the camera array 26. In some applications, a gravity vector G may be correlated to one or more of the arbitrary reference frames 280, 282, 284, and 286, as described earlier. The reference frames of different volume data sets of the same volume, such as 272 and 272', are registered with each other based on the uniquely identifiable feature of the volume in any suitable manner such as already discussed herein. The process of obtaining volume data sets of the same portion of the femur and the same portion of the pelvis can be repeated in several additional different positions, such as to define a movement cone of the hip under regular use conditions. The volume data sets 272, 276, 272', and 276' preferably are obtained using one or more ultrasound probes 32 that are tracked by the camera array 26 of the surgical navigation system 20 in a manner as described previously. In one method and system, each of the volume data sets 272, 276, 272', and 276' is obtained using only a single tracked ultrasound probe 32. In such a system, preferably there is no movement of the femur and pelvis while the volume data sets are obtained at each position. In an alternative method and system, multiple tracked ultrasound probes 32 are used simultaneously to continuously obtain simultaneous volume data sets of each anatomical structure as the patient's leg, for example, is moved in different positions. Functional motion parameters of the hip joint that are spatially related to the various volume data sets, such as a range of motion cone and the gravity vector G, may then be calculated based on the various volume data sets without the necessity of defining and/or determining local anatomical reference frames based on predefined anatomical features. Preferably, one or more computer systems 24 associated with the surgical navigation system 20 perform the required calculations and store all associated data in memory associated therewith in a manner known in the art. The same or similar functional motion analyses may be performed on other portions of the body as well in a similar manner.

Other embodiments comprising various combinations of the individual features of each of the foregoing described embodiments are specifically included herein.

INDUSTRIAL APPLICABILITY

The methods and systems described herein can facilitate the relation of information from one data set to another data set, wherein the information would not otherwise be available or easily obtainable in the other data set. The methods and systems disclosed herein in many aspects advantageously utilize arbitrarily defined unique reference frames in different data sets to easily register the data sets and relate the information from one to another without requiring identification and use of specific landmarks that can be compared and/or matched across two or more data sets. Specific procedures that may benefit from the teachings disclosed herein include surgical procedures, such as joint arthroplasty to perform functional assessments during surgery and trauma surgery to mirror information from an unaffected anatomical structure to an affected anatomical structure.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications that come within the scope of the appended claims are reserved. All patents and patent applications referred to herein are incorporated herein in the entireties thereof.

I claim:
1. A system for collecting and manipulating a volume data set of an anatomical structure, the system comprising:
    an imaging device for obtaining a first volume data set of an anatomical structure of a patient and a second volume data set of the anatomical structure; and
    a computer comprising a processing unit and a memory unit, wherein the computer is configured to:
        calculate an inherent feature of the first volume data set and the second volume data set, wherein the inherent feature has a unique position and orientation in relation to the anatomical structure that can be identified from any reference position;
        assign a first arbitrary reference frame to the first volume data set and a second arbitrary reference frame to the second volume data set;
        correlate the inherent feature to the first arbitrary reference frame;
        associate additional spatial information with the first volume data set, wherein the additional spatial infor- mation has a unique spatial relationship correlated with the first arbitrary reference frame;

register the first volume data set with the second volume data set based on the inherent feature; and correlate the additional spatial information to the second volume data set.

2. The system of claim 1, wherein the computer is further configured to determine the orientation of the anatomical structure or parts thereof with respect to a gravity vector in the first volume data set.

3. The system of claim 1, wherein the imaging device comprises an ultrasound probe.

4. The system of claim 1, wherein the computer is further configured to calculate an image moment of inertia of the first and second volume data sets.

5. The system of claim 1, wherein the computer is further configured to identify functional information in relation to the first volume data set.

6. The system of claim 1, the system further comprising a gravity sensing device configured to identify a gravity vector.

7. The system of claim 1, wherein the computer is further configured to identify movement parameters of a joint.

8. The system of claim 1, wherein the computer is further configured to calculate a unique position and orientation of a third arbitrary reference frame with respect to the first arbitrary reference frame.

9. The system of claim 1, the computer is further configured to assign the first and second arbitrary reference frames without reference to any pre-defined landmark on the anatomical structure.

10. A system for establishing a position of a portion of a bone that has been altered from a normal shape, the system comprising:

an imaging device to collect a first volume data set for a first bone that is unaltered and to collect a second volume data set of a first portion of a second bone, wherein the first volume data set includes volume data for first and second portions of the first bone; and a computer comprising a processing unit and a memory unit, wherein the computer is configured to:

identify a first unique spatial characteristic of the volume data for the first portion of the first bone;

establish a first arbitrary reference frame for the first volume data set correlated with the first unique spatial characteristic;

identify a unique spatial relation between the first arbitrary reference frame and the second portion of the first bone;

identify the second bone that normally mirrors the first bone about a centerline, wherein the second bone includes the first portion and a second portion that correspond as substantially mirror structures to the first and second portions of the first bone, respectively, and wherein the second bone has been altered from a normal shape such that the first portion of the second bone is in an altered position with regard to the second portion of the second bone;

identify a second unique spatial characteristic of the second volume data set, wherein the second unique spatial characteristic substantially mirrors the first unique spatial characteristic;

register in mirrored correlation the first volume data set with the second volume data by correlating the first unique spatial characteristic with the second unique spatial characteristic; and re-establish the normal position of the second portion of the second bone to coincide with the position of the second portion of the first bone as related to the registered position of the first portion of the first bone.

11. The system of claim 10, wherein the unique spatial relation comprises a positional vector between the volume data for the first portion of the first bone and the volume data for the second portion of the first bone.

12. The system of claim 10, wherein the system is a surgical navigation system and wherein the imaging device comprises an ultrasound probe tracked by the surgical navigation system.

13. The system of claim 12, wherein the surgical navigation system comprises a tracking device for tracking positions of each of the first and second portions of the second bone.

14. The system of claim 10, wherein the first arbitrary reference frame is established without reference to any pre-defined landmark on the anatomical structure.

15. The system of claim 10, wherein the computer is further configured to calculate an image moment of inertia of the first volume data set and the second volume data set.

16. A system for registering information associated with a first data set of an anatomical structure to a second data set of the anatomical structure, the system comprising:

an imaging device to collect the first data set of the anatomical structure and the second data set of the anatomical structure;

a computer comprising a processing unit and a memory unit, wherein the computer is configured to:

develop additional information for the first data set, wherein the additional information has a unique identifiable spatial relationship to the anatomical structure of the first data set;

establish a first arbitrary reference frame for the first data set, wherein the first arbitrary reference frame is established without reference to any pre-selected landmark on the anatomical structure and the first arbitrary reference frame has a unique spatial relationship to the first data set;

establish a second arbitrary reference frame for the second data set;

transform the first arbitrary reference frame to the second arbitrary reference frame by matching a unique spatial parameter of the first data set with the same unique spatial parameter of the second data set; and register the additional information with the second data set.

17. The system of claim 16, wherein the computer is further configured to:

calculate an inherent feature in the first data set, wherein the inherent feature has a unique position and orientation in relation to the anatomical structure that can be identified from any reference position; and correlate the inherent feature to the first arbitrary reference frame.

18. The system of claim 17, wherein the computer is further configured to:

identify the inherent feature in the second data set; and correlate the inherent feature to the second arbitrary reference frame.

19. The system of claim 17, wherein the system is a surgical navigation system, and wherein the computer is further configured to:
register the first data set with the second data set based on the inherent feature.

20. The system of claim 17, further comprising a display device,
wherein the system is configured to display the additional information in registration with the second data set on the display device; and
wherein the system is a surgical navigation system.

21. A surgical navigation system for associating spatial information related to a first volume data set of a first anatomical structure with a second volume data set of the first anatomical structure, the system comprising:
a data obtaining device, a computer, and a display device;
wherein the data obtaining device is configured to:
obtain the first volume data set of the first anatomical structure;
obtain the second volume data set of the first anatomical structure;
wherein the computer comprises a processing unit and a memory unit, wherein the computer is configured to:
assign a first arbitrary reference frame to the first volume data set;
calculate an inherent feature in the first volume data set, wherein the inherent feature has a unique position and orientation in relation to the first anatomical structure that can be identified from any reference position;
correlate the inherent feature to the first arbitrary reference frame;
associate additional spatial information with the first volume data set,
wherein the additional spatial information has a unique spatial relationship correlated with the first arbitrary reference frame;
assign a second arbitrary reference frame to the second volume data set;
identify the inherent feature in the second volume data set;
correlate the inherent feature to the second arbitrary reference frame;
register the first volume data set with the second volume data set based on the inherent feature; and
correlate the additional spatial information to the second volume data set;
wherein the display device is configured to display the additional spatial information in registration with the second volume data set on the display device.

22. The system of claim 21, wherein the computer is further configured to calculate the image moment of inertia of each of the first volume data set and the second volume data set.

23. The system of claim 21, wherein the data obtaining device comprises an ultrasound device that is tracked by the surgical navigation system.

24. The system of claim 21, wherein the computer is further configured to identify a gravity vector and correlate the gravity vector with the first arbitrary reference frame.

25. The system of claim 21, wherein the display device is configured to display the gravity vector in registration with the second volume data set.

26. The system of claim 21, wherein the data obtaining device is configured to:
obtain a third volume data set of a second anatomical structure; and
wherein the computer is further configured to:
assign a third arbitrary reference frame to the third volume data set;
calculate an inherent feature in the third volume data set, wherein the inherent feature in the third volume data set has a unique position and orientation in relation to the second anatomical structure that can be identified from any reference position;
correlate the inherent feature of the third volume data set to the third arbitrary reference frame; and
calculate a unique position and orientation of the third arbitrary reference frame with respect to the first arbitrary reference frame.

27. The system of claim 21, wherein the computer is further configured to calculate functional information about a joint between the first bone and the second bone based on the additional spatial information.

* * * * *